US009200028B2

(12) United States Patent
Bäckström et al.

(10) Patent No.: US 9,200,028 B2
(45) Date of Patent: Dec. 1, 2015

(54) STEROIDS HAVING INCREASED WATER SOLUBILITY AND RESISTANCE AGAINST METABOLISM AND METHODS FOR THEIR PRODUCTION

(71) Applicant: Umecrine Cognition AB, Solna (SE)

(72) Inventors: Torbjörn Bäckström, Umea (SE); Gianna Ragagnin, Umea (SE)

(73) Assignee: Umecrine Cognition AB, Solna (SE)

( * ) Notice: Subject to any disclaimer, the term of this patent is extended or adjusted under 35 U.S.C. 154(b) by 0 days.

(21) Appl. No.: 13/848,782

(22) Filed: Mar. 22, 2013

(65) Prior Publication Data

US 2013/0281421 A1 Oct. 24, 2013

Related U.S. Application Data

(62) Division of application No. 11/943,555, filed on Nov. 20, 2007, now Pat. No. 8,580,983.

(60) Provisional application No. 60/860,658, filed on Nov. 21, 2006.

(51) Int. Cl.

| | |
|---|---|
| ***C07J 41/00*** | (2006.01) |
| ***A61K 31/56*** | (2006.01) |
| ***C07J 7/00*** | (2006.01) |
| ***C07J 5/00*** | (2006.01) |
| ***C07J 1/00*** | (2006.01) |

(52) U.S. Cl.

CPC .. *C07J 7/002* (2013.01); *C07J 1/00* (2013.01); *C07J 1/0011* (2013.01); *C07J 5/0015* (2013.01); *C07J 7/00* (2013.01); *C07J 7/007* (2013.01); *C07J 41/00* (2013.01); *C07J 41/005* (2013.01); *C07J 41/0016* (2013.01)

(58) Field of Classification Search

CPC .................................................. C07J 41/0016
USPC .......................................... 552/519; 514/182
See application file for complete search history.

(56) References Cited

U.S. PATENT DOCUMENTS

| | | | |
|---|---|---|---|
| 3,152,121 | A | 10/1964 | Wechter |
| 5,232,917 | A | 8/1993 | Bolger et al. |
| 5,591,733 | A | 1/1997 | Bolger et al. |
| 5,925,630 | A | 7/1999 | Upasani et al. |
| 5,939,545 | A | 8/1999 | Upasani et al. |
| 6,143,736 | A | 11/2000 | Upasani et al. |
| 6,277,838 | B1 | 8/2001 | Upasani et al. |
| 7,718,639 | B2 | 5/2010 | Wulfert et al. |
| 8,114,860 | B2 | 2/2012 | Backstrom et al. |
| 2003/0060425 | A1 | 3/2003 | Ahlem et al. |
| 2003/0113284 | A1 | 6/2003 | Dalko et al. |
| 2008/0119416 | A1 | 5/2008 | Backstrom |
| 2013/0102578 | A1 | 4/2013 | Bäckström et al. |
| 2013/0102579 | A1 | 4/2013 | Bäckström et al. |
| 2014/0011779 | A1 | 1/2014 | Bäckström et al. |
| 2014/0011792 | A1 | 1/2014 | Bäckström et al. |
| 2014/0011793 | A1 | 1/2014 | Bäckström et al. |

FOREIGN PATENT DOCUMENTS

| | | |
|---|---|---|
| CZ | 294278 | 11/2004 |
| DE | 1 668 615 | 4/1972 |
| FR | 1463755 | 7/1966 |
| FR | 1463755 | 12/1966 |
| WO | WO-91/16897 A1 | 11/1991 |
| WO | 93/03732 A1 | 3/1993 |
| WO | 94/27608 | 12/1994 |
| WO | 95/21617 | 8/1995 |
| WO | 96/16076 A1 | 5/1996 |
| WO | 96/40043 | 12/1996 |
| WO | 98/05337 | 2/1998 |
| WO | 99/45931 | 9/1999 |
| WO | 99/52532 | 10/1999 |
| WO | 02/00224 A1 | 1/2002 |
| WO | WO-02/00225 A1 | 1/2002 |
| WO | 03/039554 A1 | 5/2003 |
| WO | 03/059357 | 7/2003 |
| WO | WO-2006/054938 A1 | 5/2006 |
| WO | 2011/138460 | 11/2011 |

OTHER PUBLICATIONS

Sunol, Christina et al., "Activity of B-Nor Analogues of Neurosteroids on the GABAA Receptor in Primary Neuronal Cultures", J. Med. Chem. 2006, 49, 3224-3234.
Kametani, T. et al., "Studies on the Synthesis of Heterocyclic and Natural Compounds. 95. Asymmetric Total Synthesis of (=)-Chenodeoxycholic Acid. Steroselectivity of Intramolecular Cycloaddition of Olefinic o-Quinodimethanes", J. Org. Chem. 1982, 47, 2331-2342.

(Continued)

*Primary Examiner* — Barbara P Badio
(74) *Attorney, Agent, or Firm* — McCarter & English, LLP; Steven G. Davis; Kathryn M. Kizer

(57) ABSTRACT

Steroid compounds having increased resistance against metabolism and increased water solubility are disclosed, together with methods for their production. These substances are suitable for the manufacture of pharmaceuticals for the treatment of steroid related or steroid induced CNS disorders and for use in methods of prevention, alleviation or treatment of such disorders.

2 Claims, No Drawings

(56) References Cited

OTHER PUBLICATIONS

Abstract STN 2005:294407—Kasal, Alexander et al., "Preparation of neuroactive steroids as anesthetics and anxiolytics".
Abstract STN 2006;112604—Dax, K., "Synthesis by substitution of hydroxy groups in alcohols".
McCruden, A.B., "Androgen Binding Cystosol Receptors in the Rat Thymus: Physiochemical Properties, Specificity and Localisation", Thymus, 3 (1981) 105-117.
Zeng et al., "Neurosteroid Analogues. 10. The Effect of Methyl Group Substitution at the C-6 and C-7 Positions on the GABA Modulatory and Anesthetic Actions of (3a,5a)- and (3a,5b)-3-Hydroxypregnan-20-One", Journal of Medicinal Chemistry, vol. 48, 2005, pp. 3051-3059.
Wang et al. (Aug. 2000), "The inhibitory effects of allopregnanolone and pregnenolone on the population spike, evoked in the rat hippocampal CA1 stratum pyramidale in vitro, can be blocked selectively by epiallopregnanolone," Acta Physiologica Scandinaciva 169(4):333-341.
Wang et al. (May 1, 2002), "3β-Hydroxypregnane Steroids Are Pregnenolone Sulfate-Like GABAA, Receptor Antagonosts," The Journal of Neuroscience 22(9):3366-3375.
Vippagunta et al., Advanced Drug Daily Reviews, 48 (2001), pp. 3-26.
Souillac et al., Characterization of Delivery Systems, Differential Scanning Calorimetry, pp. 217-218 (in Encyclopedia of Controlled Drug Delivery, 1999, John Wiley & Sons, pp. 212-217).
Slavikova et al., "Suppressing aggressive behavior with analogs of allogregnanolone", Steroids, pp. 99-105 (2001).
Abstract of Dax, "Synthesis by Substitution of Hydroxy Groups in Alcohols", Science of Synthesis (2006), volume date 2005, 34, pp. 71-148.
Ayres, D.C. et al., "Reduction of Steroid Ketones by Aluminum Hydride", J. Chem. Soc. B., 1970 pp. 505-510.
Slavíková, et al., "3α-Fluoro Analogues of "Allopregnanolone" and their Binding to $GABAA_A$ Receptors," Collect. Czech. Chem. Commun., 2002, pp. 30-46, vol. 67.
Crabbe, Pierre et al., Chemistry of Diflurocyclopropenes. Application to the Synthesis of Steroidal Allenes, J. Org. Chem., vol. 88, No. 8, 1973.

STEROIDS HAVING INCREASED WATER SOLUBILITY AND RESISTANCE AGAINST METABOLISM AND METHODS FOR THEIR PRODUCTION

RELATED APPLICATIONS

This application is a divisional of U.S. patent application Ser. No. 11/943,555, filed 20 Nov. 2007, which claims priority to U.S. Provisional Patent Application Ser. No. 60/860,658 filed 21 Nov. 2006, which is hereby incorporated by reference in its entirety.

FIELD OF THE INVENTION

The present invention concerns novel steroid compounds that act on the gamma-aminobutyric acid receptor-chloride ionophore ($GABA_A$-R) complex, and which can be used in the treatment of GABA and GABA-steroid related and/or steroid induced disorders of the central nervous system (CNS).

BACKGROUND OF THE INVENTION

The metabolites of progesterone, desoxycorticosterone, testosterone, androstenedione cortisone and cortisol known as androstanolones and pregnanolones have been the subject of various studies, at least partially elucidating their role in the neurological signal system in mammals. The nomenclature differs in the field and therefore the IUPAC nomenclature will be used throughout this application. The steroids inducing CNS symptoms and disorders of interest in the present application all share a common feature in comprising a 3α-hydroxy group, a 5α or 5β pregnane steroid body, and a ketone on position 20. Examples of such steroids are given in table 1:

TABLE 1

Nomenclature of the pregnanolone group

| IUPAC - nomenclature | CAS Number |
|---|---|
| 3α-hydroxy-5α-pregnan-20-one | 516-54-1 |
| 3α-hydroxy-5β-pregnan-20-one | 128-20-1 |
| 3α,21-dihydroxy-5α-pregnan-20-one | 567-02-2 |
| 3α,21-dihydroxy-5β-pregnan-20-one | 567-03-3 |
| 3α,11β,17α,21-tetrahydroxy-5β-pregnan-20-one | 53-02-1 |
| 3α-11β,17α,21-tetrahydroxy-5α-pregnan-20-one | 302-91-0 |
| 3α-17α,21-trihydroxy-5α-pregnan-11,20-dione | 547-77-3 |
| 3α-17α,21-trihydroxy-5β-pregnan-11,20-dione | 53-05-4 |

To the best knowledge of the inventors, all compounds described as novel in the description and examples are previously non-disclosed. Other steroids for the treatment of CNS disorders have however been disclosed, for example in the following documents:

U.S. Pat. No. 5,232,917 (Bolger et al.) and U.S. Pat. Nos. 5,925,630; 5,939,545; 6,143,736; 6,277,838, (Upasani et al.) disclose a number of 3α-hydroxy steroids and some 3β steroids. These patents concern the agonistic modulation of the GABA-A receptor. In other words, the patents are focused on 3α-hydroxy-steroids and their benzodiazepine like effect. All steroids that are modulators of the GABA-A receptor have the common feature of one 3α-hydroxy structure.

WO 99/45931 (Bäckström & Wang) discloses the antagonistic effect of one steroid, namely 33-OH-5α-pregnan-20-one, but is silent about the steroids described in this application.

WO 03/059357 (Bäckström et al.) discloses several 3bets-hydroxy steroids and their antagonistic effect on the GABA-A receptor but is silent about the steroids described in this application.

The antagonistic effects of 3β-OH-5α-pregnan-20-one and other 3β-OH-5α/β pregnan-steroids are disclosed by Wang et al. (Wang M. D., Bäckström T. and Landgren S. (2000) The inhibitory effects of allopregnanolone and pregnanolone on the population spike, evoked in the rat hippocampal CA1 stratum pyramidale in vitro, can be blocked selectively by epiallo-pregnanolone, *Acta Physiol Scand* 169, 333-341 and Wang M, He Y, Eisenman L N, Fields C, Zeng C M, Mathews J et al., 3β-hydroxypregnane steroids are pregnenolone sulfate-like GABA(A) receptor antagonists, *J Neurosci* 2002; 22(9):3366-75). In those papers, dose dependent antagonistic effect of 3β-OH-5α/β-pregnan-steroids and sulfatated-steroids are described. However the compounds in the present invention are not mentioned.

The present invention relates to the field of medicinal chemistry and is intended for producing compounds and compositions useful for modulation of the mammal brain excitability via the gamma-aminobutyric acid receptor-chloride ionophore ($GABA_A$-R) complex and other neurotransmitter systems which are, directly or indirectly, correlated to the $GABA_A$-R complex. It has been shown that a variety of steroidal molecules are effective in the modulation and stimulation of GABA signaling, displaying a variety of physiologic effects. The steroids comprising the components 3α-hydroxy-5α/β-pregnan-20-one have been shown to be specific GAB A-A {gamma-aminobutyric acid (A)} receptor enhancers. Due to these properties, these naturally occurring stress- and sex steroids also have adverse effects and cause certain disorders. The adverse effects of the 3α-hydroxy-pregnan-20-one-steroids are the basis for the negative CNS effects induced by these steroids. Examples of the adversive compounds are 3α-hydroxy-5α/β-pregnanolone steroids listed in table 1. Some of these steroids are very potent and have e.g. been shown to have an ability to induce anesthesia at a high pharmacological dose.

As the 3α-hydroxy-pregnane-steroids are endogenously produced and are metabolites of steroid hormones essential for life, their production cannot easily be interrupted. These steroids are produced in high amounts during several days to weeks during acute and chronic stress, the luteal phase of the menstrual cycle and during pregnancy. They are also produced within the brain. Specific blockers are therefore needed as therapy.

It has earlier been shown that certain 3β hydroxy pregnanolone steroids can block the negative brain effect of the aversive stress and sex steroids. A problem with the earlier discovered compounds is that they are easily metabolized in the body at the critical 3 position and that they are difficult to dissolve in water solution.

The direct mechanism at the receptor site has not yet been fully elucidated, due to the structural complexity of the $GABA_A$-R complex. The GABA receptor family includes several subunit compositions, of which some are known to be related to specific functions and disorders in the CNS. One aim of the present invention is thus to find new compounds that are useful in the treatment of anomaly in the excitability of GABA receptors or other neurotransmitters related to GABA receptors, in a manner which can be general or specific for some subunit compositions and functions. Disorders that are caused by the action of endogenously produced 3α-hydroxy-5α steroids or 3α-hydroxy-5β steroids on the GABA-A receptor are well characterized and understood. It is also known that 3α-hydroxy-5α/β-steroids can induce tolerance to themselves and other similar substances after exposure, and that abstinence effects occur at withdrawal of the 3α-hydroxy-5α/β-steroids. This will be further elucidated in the following:

Diseases Caused by 3α-Hydroxy-Pregna(e)n-Steroids a) Direct Action

It is established that 3α-hydroxy-5α/β-steroids can directly cause inhibition of CNS functions. Examples of disorders and symptoms caused by the direct action of 3α-hydroxy-5α/β-steroids are premenstrual dysphoric disorder, premenstrual syndrome, dementia, Alzheimer's disease, sedation, tiredness, chronic fatigue syndrome, memory disturbance, learning disturbance, disturbance of motor function, fractures, clumsiness, increased appetite and food cravings, obesity, negative mood as tension, irritability, depression, decreased hearing and eye sight, worsening of Petit Mal epilepsy, burn out syndrome.

b) Tolerance

Continuous and long exposure to 3α-hydroxy-5α/β-steroids causes a malfunctioning of the GABA-A receptor system. A tolerance develops and this tolerance is the initial step in a process that ultimately leads to stress sensitivity, concentration difficulties, and loss of impulse control and depression. The action of 3α-hydroxy-5α/β-steroids have been found to be a factor which reinforces drug dependency. This has been the focus of extensive research.

c) Abstinence

A continuous but shorter exposure to 3α-hydroxy-5α/β-steroids results in a withdrawal effect when the exposure is ended. This phenomenon occurs i.e. during menstruation when the production of 3α-hydroxy-5α/β-steroids by the corpus luteum of the ovary is interrupted. This withdrawal phenomenon also occurs after giving birth (post partum) when the 3α-hydroxy-5α/β-steroid production by the placenta is interrupted. The same phenomenon is also noted when a period of stress is ended. As a response to stress, the adrenals have produced 3α-hydroxy-5α/β-steroids. When this production is interrupted, withdrawal symptoms may occur. Examples of conditions that are influenced by this withdrawal/abstinence phenomenon are partial epilepsy where the patient has an epileptic focus in the cerebral cortex where a worsening occurs at the withdrawal period during menstruation. This phenomenon is called "catamenial epilepsy". Other examples are menstrual related migraine and stress related migraine, mood changes post partum and weekend headache. Abstinence is a sign of an earlier developed tolerance.

In view of the above, it is clear that steroids are important drug candidates. Naturally occurring steroids are however subject to intense metabolism and are therefore usually not suitable for oral administration. Also in other routes of administration the metabolism is high and makes it impossible to use the compounds as medication and treatments as the active parts of the compounds are first destroyed by the metabolism.

A second problem with steroid compounds is that they are difficult to solute in water solutions and therefore difficult to administer in vivo.

These problems and others are solved by compounds according to the present invention.

SUMMARY OF THE INVENTION

The present inventors have synthesized new compounds that are protected against metabolism in the 3 position of the steroid. Surprisingly, these compounds also have increased water solubility, due to their modified structural features. The inventors do not wish to be bound to any theory, but it is assumed that the advantageous properties of the novel compounds are due to the presence of a double bond in the steroid core, and the replacement of a keto group with an oxime group at positions 20, 21 or 17 respectively in the mentioned scaffolds of pregnane, pregnene, androstane and androstene series.

In summary, it is known that 3α-hydroxy-delta 4-5, 5α/β-steroids cause CNS disorders through the above mentioned three possible mechanisms: a) direct action, b) tolerance induction, and c) withdrawal effect. The compounds made available through the embodiments of the present invention belong to the pregnane-, pregnene-, androstane-androstene-series, with the addition of suitable functionalities. The compounds can be used alone or as prodrugs and/or in combination with formulations and other compositions in order to enhance and modulate the effects on CNS. Compositions within the scope of this invention include all compositions wherein the compounds of this invention are contained in an amount that is effective to achieve the intended purposes.

To the best knowledge of the present inventors, this is the first time steroid compounds with increased resistance against metabolism and increased water solubility are disclosed. In addition, these substances are suggested for the manufacture of pharmaceuticals for the treatment of many specific steroid related or steroid induced CNS disorders and for use in methods of treatment, according to the attached claims which are incorporated herein by reference.

DETAILED DESCRIPTION OF THE INVENTION

The invention concerns new compounds, with protection against metabolism and with increased water solubility, and methods of producing such compounds with antagonistic and blocking effects of the 3α-hydroxy-pregna(e)n-steroid induced CNS disorders. The present invention is based on the discovery that steroids represented by the formulae I or II have an effect as modulators of the GABA receptor signaling as agonists, antagonists or inverse agonists.

The inventors have shown that the presence of a tertiary alcohol moiety in position 3 prolongs the half-life of a steroidal compound within the body through preventing metabolic oxidations or degradation in the body. The presence of a hydrogen-bond acceptor/donator group bonded to the D ring of a steroidal molecule influences the ability of the steroid to modulate the GABA receptor signaling.

The present invention relates to novel steroids represented by the formulae I or II, and pharmaceutically acceptable derivatives, salts, prodrugs or solvates thereof:

I

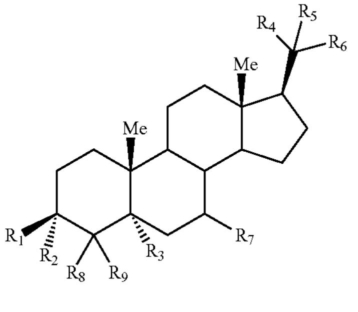

-continued

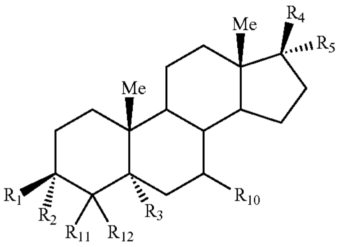

II wherein $R_1$ is chosen among an ethynyl, ethenyl, ethyl, or other saturated or unsaturated alkyl groups; hydroxyl, in its free form or combined with carboxylic acid residues, sugars, alkyl groups to form esters or ether or glycosylated compounds; fluorine or other halogens; a proton;

$R_2$ is chosen among an ethynyl, ethenyl, ethyl, or other saturated or unsaturated alkyl groups; hydroxyl, in its free form or combined with carboxylic acid residues, sugars, alkyl groups to form esters or ether or glycosylated compounds; fluorine or other halogens; a proton;

$R_3$ is 5α- or 5β-H $R_4$ is a nitro, hydroxyl, free or bonded with an ester, ether, sugar; and $R_5$ is a proton.

According to an embodiment of the invention, the compounds are steroids represented by the above formulae I or II, and pharmaceutically acceptable derivatives, salts, prodrugs or solvates thereof, wherein $R_4$, $R_5$ is =O or N as oxime =NOH, or a homo- or heterocycle;

$R_6$ is a methyl, an alkyl group or —$CH_2OR$ where R is H, a carboxylic acid residue, an alkyl group or a sugar; —$CH_2X$ where X is fluorine or another halogen;

$R_7$, $R_{10}$ is OH, $CH_3$ or H at the seven position.

$R_8$, $R_9$ or $R_{11}$, $R_{12}$ represent two Me— groups, or Me- and H, respectively, or two —H.

According to an embodiment $R_7$, $R_{10}$ is OH or $CH_3$ at the seven position.

According to an embodiment of the invention, the compounds are steroids represented by the above formula I, or a pharmaceutically acceptable salt thereof, wherein $R_1$ is an ethynyl group; hydroxyl, in its free form or combined with carboxylic acid residues; fluorine; or a proton; $R_2$ is an ethynyl group; hydroxyl, in its free form or combined with carboxylic acid residues; fluorine; or a proton; $R_3$ is 5α- or 5β-H; $R_4$ is hydroxyl and $R_5$ a proton, or $R_4$, $R_5$ together is O or N as oxime =NOH; $R_6$ is a methyl group; $R_7$ is H; and $R_8$=$R_9$=methyl or H.

According to an embodiment of the invention, the compounds are steroids represented by the above formula II, or a pharmaceutically acceptable salt thereof, wherein $R_1$ is an ethynyl group or hydroxyl; $R_2$ is an ethynyl group or hydroxyl; $R_3$ is 5α- or 5β-H; $R_4$ and $R_5$ together is O or N as oxime =NOH; $R_{10}$ is H; and $R_{11}$=$R_{12}$=H.

According to an embodiment, an unsaturation can be present between C4-C5 or C5-C6 or at other positions in the molecule. $R_8$, $R_9$ or $R_{11}$, $R_{12}$ represent two Me— groups, or Me- and H, respectively, or two —H, or if said unsaturation is between C4-C5, then one of $R_8$, $R_9$ or $R_{11}$, $R_{12}$, respectively, is Me- or H while the other one is absent. According to one aspect of this embodiment, the compounds are steroids represented by the above formula I, wherein $R_1$ is an ethynyl group or hydroxyl; $R_2$ is an ethynyl group or hydroxyl; $R_3$ is absent; $R_4$ is hydroxyl; $R_5$ a proton; or $R_4$ and $R_5$ is together =O or N as oxime =NOH; $R_6$ is a methyl group; $R_7$ is H; and $R_8$, $R_{11}$ is methyl or H; and $R_9$, $R_{12}$ is methyl, H, or, if said unsaturation is between C4-C5, absent.

The compounds of formula I and II may exist as optical isomers; consequently the invention includes all individual isomers that may be separated by common chromatographic techniques as well as other known separation methods known by those skilled in the art.

The present invention also encompasses all functionally equivalent derivatives and prodrugs where esters and ethers have been added to the hydroxyl groups of the steroids. Examples of suitable derivatives include, but are not limited to, sulphates, formates, acetates, propionates, glycosilations with sugars or oligosaccharides, methylates, ethylates. One skilled in the art can recognize that other functional groups not included in this list of examples can be employed.

Tables 2 and 3 show examples of the structure of a series of compounds according to the invention, were the 3-hydroxy position of the pregnane, pregnene, androstane or androstene steroid structure is protected against metabolism in 3-position with an ethynyl, ethenyl or acetate structure added to the steroid molecule or the hydroxyl group replaced with a fluorine atom.

TABLE 2

| New Compounds with metabolism protection based on formula I | |
|---|---|
| UC2005 | 3α-ethynyl, 3β-hydroxyl, 5β-pregnan-20-one |
| 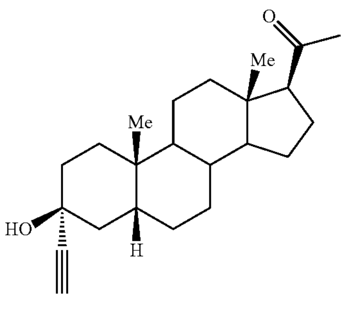 | |

TABLE 2-continued
| New Compounds with metabolism protection based on formula I | | |
|---|---|---|
| UC2007 | 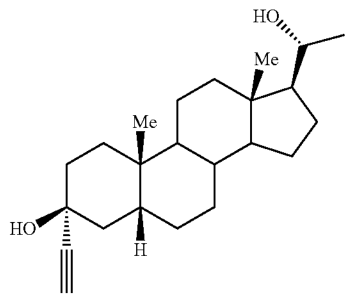 | 3α-ethynyl, 5β-pregnan-3β, 20(R)-diol |
| UC2009 | 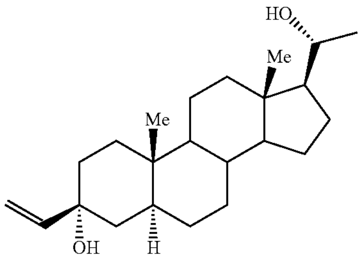 [SMILES: C=C[C@@]1(O)CC[C@]2(C)C3CC[C@@]4(C)C(CC[C@@H]4[C@@H](C)O)C3CC[C@H]2C1] | 3β-ethenyl, 5α-pregnan-3α, 20(R)-diol |
| UC2012 | 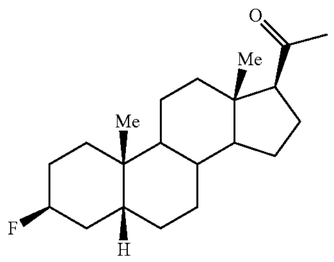 [SMILES: CC(=O)[C@H]1CCC2C3CC[C@@H]4C[C@@H](F)CC[C@]4(C)C3CC[C@@]21C] | 3β-fluor, 5β-pregnan-20-one |
| UC2013 | 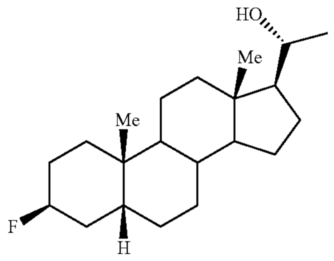 [SMILES: C[C@@H](O)[C@H]1CCC2C3CC[C@@H]4C[C@@H](F)CC[C@]4(C)C3CC[C@@]21C] | 3β-fluor, 5β-pregnan-20-(R)-ol |
| UC2014 | 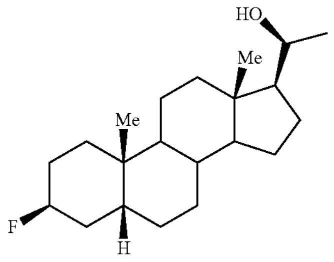 [SMILES: C[C@H](O)[C@H]1CCC2C3CC[C@@H]4C[C@@H](F)CC[C@]4(C)C3CC[C@@]21C] | 3β-fluor, 5β-pregnan-20-(S)-ol |

TABLE 2-continued
| New Compounds with metabolism protection based on formula I | | |
|---|---|---|
| UC2016 | 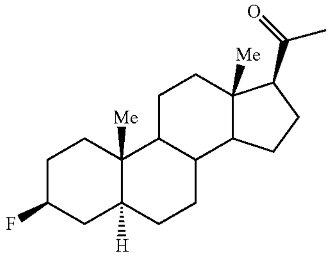 [SMILES: CC(=O)[C@H]1CCC2C3CC[C@H]4C[C@@H](F)CC[C@]4(C)C3CC[C@@]21C] | 3β-fluor, 5α-pregnan-20-one |
| UC2017 | 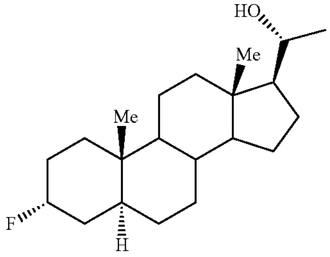 [SMILES: C[C@@H](O)[C@H]1CCC2C3CC[C@H]4C[C@H](F)CC[C@]4(C)C3CC[C@@]21C] | 3α-fluor, 5α-pregnan-20-(R)-ol |
| UC2018 | 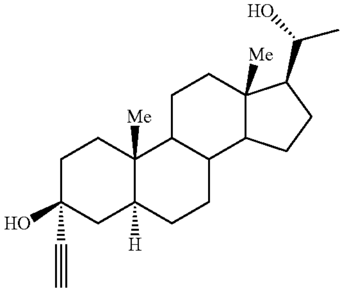 [SMILES: C#C[C@]1(O)CC[C@]2(C)C3CC[C@@]4(C)C(CC[C@@H]4[C@@H](C)O)C3CC[C@H]2C1] | 3α-ethynyl, 5α-pregnan-3β, 20(R)-diol |
| UC2019 | 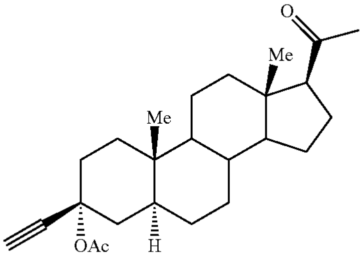 [SMILES: C#C[C@@]1(OC(C)=O)CC[C@]2(C)C3CC[C@@]4(C)C(CC[C@@H]4C(C)=O)C3CC[C@H]2C1] | 3β-ethynyl, 3α-acetyl, 5α-pregnan-20-one |
| UC2024 | 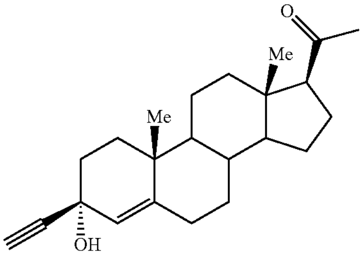 [SMILES: C#C[C@]1(O)C=C2CCC3C(CC[C@@]4(C)C3CC[C@@H]4C(C)=O)[C@@]2(C)CC1] | 3β-ethynyl, 3α-hydroxyl, Δ4-pregnen-20-one |

TABLE 2-continued
| New Compounds with metabolism protection based on formula I | | |
|---|---|---|
| UC2026 | 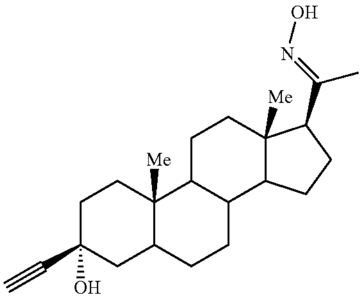 [SMILES: C#C[C@@]1(O)CC[C@@]2(C)C(CCC3C2CC[C@@]2(C)C3CC[C@@H]2/C(C)=N/O)C1] | 3β-ethynyl, 3α-hydroxyl, 5α-pregnan-20-one oxime |
| UC2029 | 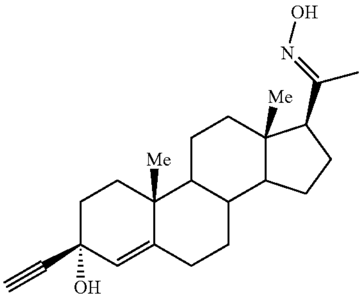 [SMILES: C#C[C@]1(O)C=C2CCC3C(CC[C@@]4(C)C3CC[C@@H]4/C(C)=N/O)[C@@]2(C)CC1] | 3β-ethynyl, 3α-hydroxyl, Δ4-pregnen-20-one oxime |
| UC2030 | 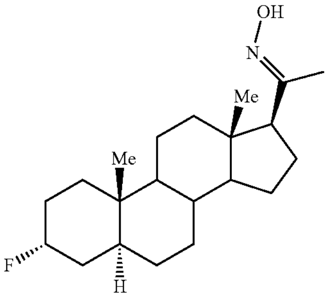 [SMILES: C/C(=N\O)[C@H]1CCC2C3CC[C@H]4C[C@H](F)CC[C@]4(C)C3CC[C@@]21C] | 3α-fluor, 5α-pregnan-20-one oxime |
| UC2032 | 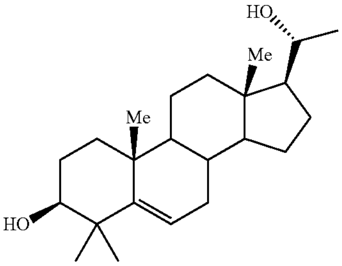 [SMILES: C[C@@H](O)[C@H]1CCC2C3CC=C4C(C)(C)[C@@H](O)CC[C@]4(C)C3CC[C@@]21C] | 3-dimethyl, Δ5-pregnen-3β, 20(R)-diol |
| UC2034 | 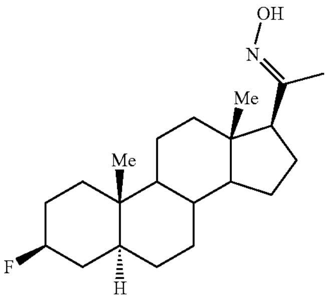 [SMILES: C/C(=N\O)[C@H]1CCC2C3CC[C@H]4C[C@@H](F)CC[C@]4(C)C3CC[C@@]21C] | 3β-fluor, 5α-pregnan-20-one oxime |

TABLE 3

| New Compounds with metabolism protection based on formula II | | |
|---|---|---|
| UC2021 | 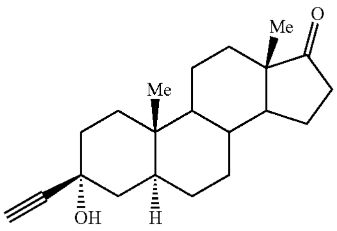 [SMILES: C#C[C@@]1(O)CC[C@]2(C)C3CC[C@]4(C)C(=O)CCC4C3CC[C@H]2C1] | 3β-ethynyl, 3α-hydroxyl, androstan-17-one |
| UC2025 | 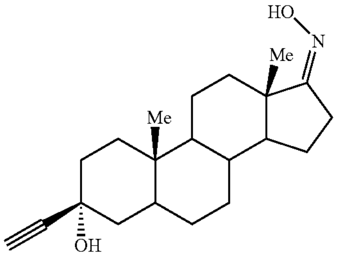 [SMILES: C#C[C@@]1(O)CC[C@@]2(C)C(CCC3C2CC[C@]2(C)/C(=N\O)CCC32)C1] | 3β-ethynyl, 3α-hydroxyl, androstan-17-one oxime |
| UC2027 | 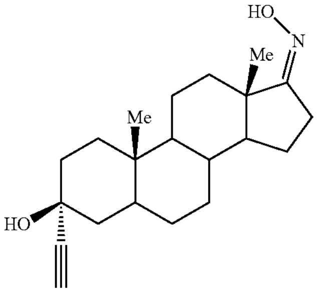 [SMILES: C#C[C@]1(O)CC[C@@]2(C)C(CCC3C2CC[C@]2(C)/C(=N\O)CCC32)C1] | 3α-ethynyl, 3β-hydroxyl, androstan-17-one oxime |

In Table 4 are shown examples of structures of a series of compounds where the water solubility is increased relative to the 5-saturated compound (UC2024) and where the water solubility is increased by adding an oxime group relative to a keto group or simple hydroxy group (UC2027, UC2029).

TABLE 4

| Examples of new compounds with increased water solubility | | |
|---|---|---|
| UC2013 | 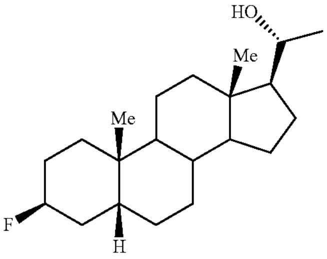 [SMILES: C[C@@H](O)[C@H]1CCC2C3CC[C@@H]4C[C@@H](F)CC[C@]4(C)C3CC[C@@]21C] | 3β-fluor, 5β-pregnan-20-(R)-ol |
| UC2014 | 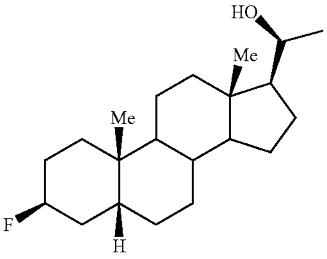 [SMILES: C[C@H](O)[C@H]1CCC2C3CC[C@@H]4C[C@@H](F)CC[C@]4(C)C3CC[C@@]21C] | 3β-fluor, 5β-pregnan-20-(S)-ol |

TABLE 4-continued
| Examples of new compounds with increased water solubility | | |
|---|---|---|
| UC2017 | 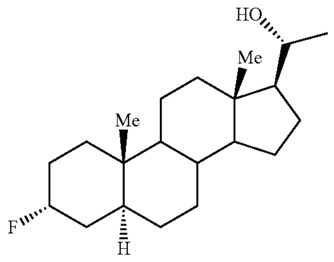 [SMILES: C[C@@H](O)[C@H]1CCC2C3CC[C@H]4C[C@H](F)CC[C@]4(C)C3CC[C@@]21C] | 3α-fluor, 5α-pregnan-20-(R)-ol |
| UC2018 | 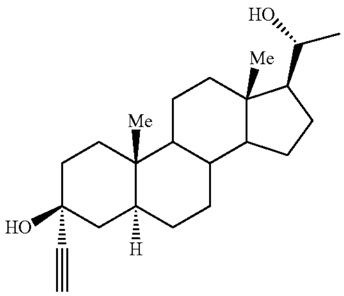 [SMILES: C#C[C@]1(O)CC[C@]2(C)C3CC[C@@]4(C)C(CC[C@@H]4[C@@H](C)O)C3CC[C@H]2C1] | 3α-ethynyl, 5α-pregnan-3β, 20(R)-diol |
| UC2024 | 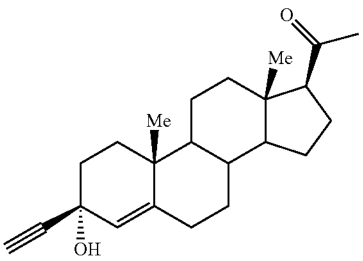 [SMILES: C#C[C@]1(O)C=C2CCC3C(CC[C@@]4(C)C3CC[C@@H]4C(C)=O)[C@@]2(C)CC1] | 3β-ethynyl, 3α-hydroxyl, Δ4-pregnen-20-one |
| UC2027 | 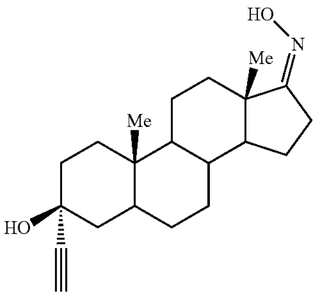 [SMILES: C#C[C@]1(O)CC[C@@]2(C)C(CCC3C2CC[C@]2(C)/C(=N\O)CCC32)C1] | 3α-ethynyl, 3β-hydroxyl, androstan-17-oxime |
| UC2029 | 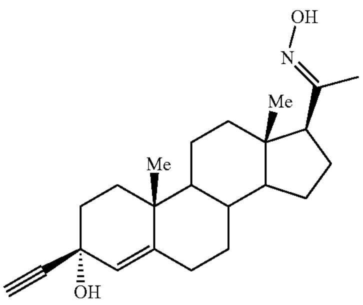 [SMILES: C#C[C@]1(O)C=C2CCC3C(CC[C@@]4(C)C3CC[C@@H]4/C(C)=N/O)[C@@]2(C)CC1] | 3β-ethynyl, 3α-hydroxyl, Δ4-pregnen-20-oxime |

TABLE 4-continued

| Examples of new compounds with increased water solubility | | |
|---|---|---|
| UC2030 | 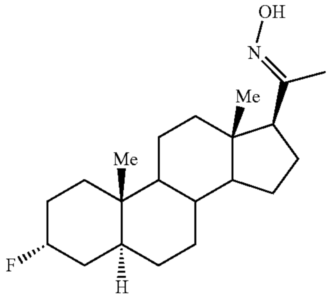 [SMILES: C/C(=N\O)[C@H]1CCC2C3CC[C@H]4C[C@H](F)CC[C@]4(C)C3CC[C@@]21C] | 3α-fluor, 5α-pregnan-20-oxime |
| UC2032 | 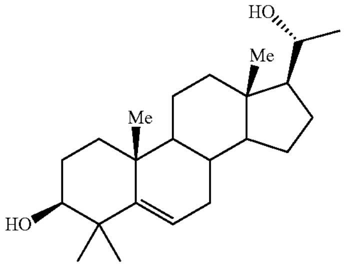 [SMILES: C[C@@H](O)[C@H]1CCC2C3CC=C4C(C)(C)[C@@H](O)CC[C@]4(C)C3CC[C@@]21C] | 3-dimethyl, Δ5-pregnen-3β, 20(R)-diol |
| UC2034 | 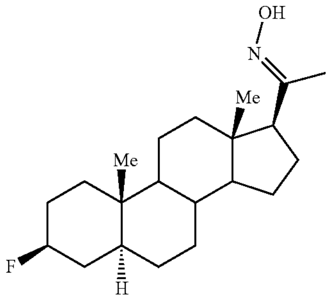 [SMILES: C/C(=N\O)[C@H]1CCC2C3CC[C@H]4C[C@@H](F)CC[C@]4(C)C3CC[C@@]21C] | 3β-fluor, 5α-pregnan-20-one oxime |

HPLC Retention Times [Min] for Compounds According to the Invention

HPLC Conditions:

HPLC System (Waters) Column Symmetry® $C_{18}$ 3.5 μm 4.6×75 mm (Waters); T: 45° C.; flow 1.0 mL/min; isocratic eluent conditions 40:60 v/v $H_2O$:MeOH. Injection volume: 100 μL.

Solvents used for eluent are of HPLC grade, water filtered through a Millipore apparatus; all solvents were filtered through a 0.45 μm Millipore filter and degassed by $N_2$ stream prior use.

Since the analyses are carried in reverse phase, shorter retention times correspond to higher hydrophilicity.

TABLE 5

| Reference substances: | retention time [min] |
|---|---|
| 3β-5β-pregnan-20-one | 24.4 |
| 3β-5α-pregnan-20-one | 30.0 |

TABLE 6

| Inventive compounds: | retention time [min] |
|---|---|
| UC 2021 | 7.8 |
| UC 2024 | 14.0 |

TABLE 6-continued

| Inventive compounds: | retention time [min] |
|---|---|
| UC 2025 | 13.9 |
| UC 2026 | 16.9 |

As seen above in Tables 5 and 6 the retention times for the inventive compounds are shorter than for the reference compounds, indicating that the former have higher hydrophilicity than the latter.

The synthesis, the separation and the identification of the compounds in this invention can be performed using method steps known as such by those skilled in the art.

The present inventors have surprisingly found that the reaction of the ethynyl Grignard reagent with 3, 20/17 diketone steroids is in the most cases selective for the position 3 and no protection/deprotection for the other ketone functionality was required. Both α and β isomers are formed, which can be separated by chromatographic methods and recrystallization.

The starting materials for the compounds described in the present invention are the corresponding steroids with a 3-hydroxyl substituent and a keto group in positions 20 or 17. They can be converted into the respective diones by oxidation with IBX reagent. The reaction proceeds smoothly and with complete conversion. Other suitable steroids can be employed as starting material when required.

The reactions are carried out in a suitable solvent such as methanol, ethanol, water, THF, diethyl ether, dichloromethane or other solvents or mixture of solvents that one skilled in the art can recognize as suitable.

The reactants are chosen in order to avoid, when possible, use of reactants, such as heavy metals, which are toxic even in traces or are difficult to be completely removed in the workup procedure.

Reactions involving air or moisture sensitive reagents or products are carried out under inert atmosphere, such as nitrogen or argon gas, in the presence of dry solvents. Diethyl ether and tetrahydrofuran are dried over Na in the presence of benzophenone. Syringes purged with inert gas were used for the transfer of reagents and dry solvents. Optimized reaction conditions, such as time and temperature, were determined by monitoring the formation of products and the loss of starting material using a suitable chromatographic technique such as TLC or GC/MS.

Purifications are carried out by using chromatographic techniques such as flash silica chromatography or preparative high performance liquid chromatography (HPLC) by using a HPLC apparatus. Those skilled in the art can recognize that alternative purification methods can be employed, and laboratory chromatographic techniques can be adapted to industrial scale by using chromatographic columns for scaled preparations.

Identification of the products is carried out by using suitable analytical techniques such as 1H-NMR, 13C-NMR, mass spectrometry, IR spectroscopy and any other assay that one skilled in the art would recognize as suitable for structural identification and purity determination of the compounds in the present invention.

The compounds according to the invention have inter alia the advantage of being both protected against metabolism, and more easily water soluble. The method of synthesis has the advantage of consisting of steps known as such, and is comparatively easy—once disclosed—to use.

The following examples of steroids in the present invention are provided. The examples are illustrative, but not limiting, of the methods and compositions of the present invention. One skilled in the art will recognize that similar reagents, solvents, conditions and parameters can be used in the reactions, depending on the substrate. NMR data were recorded using a Bruker 400 MHz spectrometer.

EXAMPLES

Examples Based on Formula I

Example 1

UC2016-3β-fluor, 5α-pregnan-20-one

3α-OH 5α-pregnan-20-one (3 mmol), was dissolved in 20 mL dry dichloromethane under $N_2$ atmosphere. DAST (700 mg, 4.33 mmol) was added slowly dropwise at room temperature (rt) and the resulting yellowish solution was left stirring at rt for 1 h. Reaction was followed by TLC. The solution was quenched by slow addition of a 5% $NaHCO_3$ solution (60 mL). The water phase was extracted with dichloromethane (3×20 mL), the organic phases collected dried over $MgSO_4$ and the solvent removed under reduced pressure, yielding a yellowish oil which was purified by silica flash column chromatography (pentane:ethyl acetate 9:1). Products are, in the order: elimination of $H_2O$ at 2,3 positions (yield: 67%); fluorination at 3-OH with inversion of configuration 30% (UC2016); fluorination at 3-OH with retention of configuration (3%-traces). 1H NMR (400 MHz, $CDCl_3$-d6): δ 4.57-4.37 (dm, 1H); 2.51 (t, 1H); 2.12 (m, 1H); 2.11 (s, 3H); 2.02-1.99 (m, 2H); 0.83 (s, 3H); 0.67 (m, 1H); 0.61 (s, 3H).

Example 2

UC2018-3α-ethynyl, 5α-pregnan-3β,20(R)-diol

3α-ethynyl, 3β-hydroxy, 5α-pregnan-20-one (0.3 mmol) was dissolved in a solution of 2 mL dichloromethane and 5 mL MeOH at rt, in a flask with outlet to air. $NaBH_4$ (2.1 equiv.) was added in one portion and the suspension left stirring for 3 h at rt. The colorless solution was evaporated in vacuum, yielding a white residue which was extracted with 20+20 mL $H_2O$ diethyl ether. The aqueous phase was extracted with 30 mL dichloromethane: diethyl ether 1:1, the organic phases collected, dried over $MgSO_4$, and the solvents removed under vacuum. The white solid was purified by silica flash column chromatography (1:4 diethyl ether:dichloromethane), Quantitative overall yield. The product with (R)-configuration at 20-C is the main product (90%), as determined by NMR measurements.

$^1H$ NMR (400 MHz, $CDCl_3$-d6): δ 3.72 (m, 1H); 2.49 (s, 1H); 2.02 (m, 1H); 1.86 (2m, 2H); 1.12 (d, 3H); 0.80 (s, 3H); 0.74 (s, 3H).

Example 3

UC2019-3β-ethynyl, 5α-pregnan-20-one 3α-acetate

3β-ethynyl, 3α-hydroxy, 5α-pregnan-20-one (0.25 mmol) and pyridine (2 equiv.) were dissolved in dry dichloromethane, followed by the dropwise addition of acetic anhydride (4 equiv.) at rt under nitrogen atmosphere.

The mixture was left stirring at 40° C. under three days. The dark mixture was quenched by the addition of 50 mL HCl 10%, then washed with a $NaHCO_3$ 10% aqueous solution (2×30 mL) until pH=7. The organic phase was collected, dried over $MgSO_4$, and concentrated. The yellowish residue was purified by silica flash column chromatography (1:4 diethyl ether: dichloromethane) to afford the ester in 87% yield.

1H NMR (400 MHz, CDCl3-d6):δ 2.60 (s, 1H); 2.51 (t, 1H); 2.43 (m, 1H); 2.11 (s, 3H); 2.03 (s, 3H); 0.82 (s, 3H); 0.60 (s, 3H).

Example 4

UC2024-3β-ethynyl, 3α-hydroxyl, Δ-4-pregnen-20-one

Progesterone (1 mmol) was dissolved in 25 mL dry THF at rt under nitrogen. Ethynyl magnesium bromide (1.1 equiv.) was added dropwise at rt under stirring and the solution was left stirring overnight at rt under nitrogen. The yellowish solution was then quenched with saturated $NH_4Cl_{(aq)}$ and the aqueous phase extracted with dichloromethane (3×30 mL). The collected organic phases were evaporated under reduced pressure, the resulting yellow oil dissolved in dichloromethane, washed with brine and dried over $MgSO_4$. The solution was reduced under vacuum, and the residue purified by silica flash column chromatography (1:4 diethylether: dichloromethane), typical yields 30%.

$^1$H NMR (400 MHz, $CDCl_3$-d6): δ 5.32 (s, 1H); 2.51 (m, 2H); 2.14 (m, 2H); 2.11 (s, 3H); 1.05 (s, 3H); 0.64 (s, 3H).

Example 5

UC2026-3β-ethynyl, 3α-hydroxyl, 5α-pregnan-20-one oxime

3β-ethynyl, 3α-hydroxyl, 5α-pregnan-20-one 3,20-5c-pregnandione (1.580 g, 5.0 mmol) was dissolved in 50 mL dry THF at rt under nitrogen. Ethynyl magnesium bromide (1.1 equiv) was added dropwise at rt under stirring and the solution was left stifling overnight at rt under nitrogen flow. The yellowish solution was then quenched with saturated $NH_4Cl$(aq) and the aqueous phase extracted with dichloromethane (3×30 mL). The collected organic phases were evaporated under reduced pressure, the resulting yellow oil dissolved in dichloromethane, washed with brine and dried over $MgSO_4$. The solution was reduced under vacuum, and the residue purified by silica flash column chromatography (1:4 diethylether:dichloromethane), typical yields 13%. Eventual traces of byproducts can be eliminated by further recrystallization from diethylether.

1H NMR (400 MHz, CDCl3-d6): δ 2.51 (t, 1H); 2.43 (s, 3H); 2.14 (m, 1H); 2.11 (s, 3H); 0.81 (s, 1H); 0.60 (s, 3H).

3α-ethynyl, 3β-hydroxyl, 5α-pregnan-20-one

Was obtained as a byproduct from the above described reaction and separated by silica flash column chromatography. Typical yield 72%.

1H NMR (400 MHz, CDCl3-d6): δ 2.52 (t, 1H); 2.47 (s, 1H); 2.11 (s, 3H); 0.80 (s, 3H), 0.60 (s, 3H).

3β-ethynyl, 3α-hydroxyl, 5α-pregnan-20-one oxime

3β-ethynyl, 3α-hydroxyl, 5α-pregnan-20-one (10 mmol) is dissolved in dichloromethane 5 mL and ethanol 50 mL at rt and air atmosphere, in a 250 mL round bottom flask. 4 equiv. of $NH_2OH$ chlorhydrate and 4 equiv. of sodium acetate are dissolved in 5 mL $H_2O$ and then added to the steroid solution. 20 mL of ethanol are added and the mixture put on reflux overnight. The mixture is then cooled and the solvent removed under reduced pressure. The white residue is then treated with 50 mL $H_2O$ and 50 mL dichloromethane, the aqueous phase extracted with 3×30 mL dichloromethane. The collected organic phases are then dried over $MgSO_4$, filtrated and the solvent removed under reduced pressure. The final residue is purified by silica flash column chromatography dichloromethane:diethyl ether 4:1, typical yields 95-100%.

1H NMR (400 MHz, CDCl3-d6): δ 2.43 (s, 1H); 2.22 (t, 1H); 2.05 (m, 1H); 1.88 (s, 3H); 1.86 (m, 1H); 0.81 (s, 3H), 0.62 (s, 3H).

Example 6

UC2029-3β-ethynyl, 3α-hydroxyl, Δ4-pregnen-20-one oxime

3β-ethynyl, 3α-hydroxyl, Δ4-pregnen-20-one (10 mmol) is dissolved in dichloromethane 5 mL and ethanol 50 mL at rt and air atmosphere, in a 250 mL round bottom flask. 4 equiv. of $NH_2OH$ chlorhydrate and 4 equiv. of sodium acetate are dissolved in 5 mL $H_2O$ and then added to the steroid solution. 20 mL of ethanol are added and the mixture put on reflux overnight. The mixture is then cooled and the solvent removed under reduced pressure. The white residue is then treated with 50 mL $H_2O$ and 50 mL dichloromethane, the aqueous phase extracted with 3×30 mL dichloromethane. The collected organic phases are then dried over $MgSO_4$, filtrated and the solvent removed under reduced pressure. The final residue is purified by silica flash column chromatography dichloromethane:diethyl ether 4:1, typical yields 85%.

$^1$H NMR (400 MHz, $CDCl_3$-d6): δ 5.32 (s, 1H); 2.51 (s, 1H); 2.19 (m, 2H); 2.06 (m, 1H); 1.88 (s, 3H); 2.03 (s, 3H); 1.05 (s, 3H); 0.65 (s, 3H).

Example 7

UC2030-3α-fluor, 5α-pregnan-20-one oxime

3α-fluor, 5α-pregnan-20-one

3α-OH 5α-pregnan-20-one (3 mmol), was dissolved in 20 mL dry dichloromethane under $N_2$ atmosphere. DAST (700 mg, 4.33 mmol) was added slowly dropwise at −78° C. and the resulting yellowish solution was left stirring at rt for 1 h. Reaction was followed by TLC. The solution was quenched by careful addition of a 5% $NaHCO_3$ solution (60 mL). The water phase was extracted with dichloromethane (3×20 mL), the organic phases collected dried over $MgSO_4$ and the solvent removed under reduced pressure, yielding a yellowish oil which was purified by silica flash column chromatography (pentane:ethyl acetate 9:1). Products are, in the order: elimination of $H_2O$ at 2,3 positions (yield: 67%); fluorination at 3-OH with inversion of configuration 30%; fluorination at 3-OH with retention of configuration (3%-traces).

1H NMR (400 MHz, $CDCl_3$-d6): δ 4.87-4.75 (d, 1H); 2.53 (t, 1H); 2.11 (s, 3H); 2.00 (m, 1H); 0.95 (m, 1H); 0.80 (m, 1H); 0.78 (s, 3H); 0.60 (s, 3H).

3α-fluor, 5α-pregnan-20-one oxime

3α-fluor, 5α-pregnan-20-one (10 mmol) is dissolved in dichloromethane 5 mL and ethanol 50 mL at rt and air atmosphere, in a 250 mL round bottom flask. 4 equiv. of $NH_2OH$ chlorhydrate and 4 equiv. of sodium acetate are dissolved in 5 mL $H_2O$ and then added to the steroid solution. 20 mL of ethanol are added and the mixture put on reflux overnight. The mixture is then cooled and the solvent removed under reduced pressure. The white residue is then treated with 50 mL $H_2O$ and 50 mL dichloromethane, the aqueous phase extracted with 3×30 mL dichloromethane. The collected organic phases are then dried over $MgSO_4$, filtrated and the solvent removed under reduced pressure. The final residue is purified by silica flash column chromatography (dichloromethane:diethyl ether 4:1). Quantitative yield.

$^1$H NMR (400 MHz, $CDCl_3$-d6): δ 4.90-4.78 (d, 1H); 2.26 (t, 1H); 2.10 (m, 1H); 1.90 (s, 3H); 0.98 (m, 1H); 0.82 (s, 3H); 0.65 (s, 3H).

Example 8

UC2034-3β-fluor, 5α-pregnan-20-one oxime

Was obtained by using the same synthetic protocol as Example 7 for UC2030 starting from the corresponding 3β-fluor, 5α-pregnan-20-one isomer.

Example 9

UC2032-3-dimethyl, Δ5-pregnen-3β,20(R)-diol 3-dimethyl, Δ5-pregnen-3,20-dione 525 mg progesterone are dissolved in 10 mL dry toluene at rt. 3.4 mL (2 equiv.) of a 1.0 M solution of sodium t-buthylate in dry toluene is added dropwise to the progesterone solution, under stirring and $N_2$ atmosphere. The yellowish solution is let stirring in 20 min 2 equiv. of MeI are then added dropwise to the mixture, which is stirred overnight at rt under $N_2$. The mixture is quenched with 10 mL water and 10 mL dichloromethane, the aqueous phase extracted with 2×30 mL dichloromethane. The organic phases are collected, dried over MgSO4, the solvent removed under vacuum yielding a yellowish residue, which is purified by silica flash column chromatography (1:4 diethyl ether:dichloromethane). A further purification of the desired fraction is performed by silica flash column chromatography (1:9 ethyl acetate:pentane). Yield: 25%.

$^1$H NMR (400 MHz, $CDCl_3$-$d_6$): δ 155.56 (m, 1H); 2.54 (m, 3H); 2.13 (s, 3H); 1.23 (s, 6H); 0.86 (s, 3H); 0.64 (s, 3H).

3-dimethyl, Δ5-pregnen-3β,20(R)-diol 91 mg of 3-dimethyl, Δ5-pregnen-3,20-dione are dissolved in 3.0 mL dichloromethane and 15 mL MeOH at rt, in a flask with outlet to air. $NaBH_4$ (2.1 equiv.) is added in one portion and the suspension left stirring for 6 h at rt. The colorless solution was evaporated in vacuum, yielding a white residue which was extracted with 20+20 mL $H_2O$ diethyl ether. The aqueous phase was extracted with 30 mL dichloromethane: diethyl ether 1:1, the organic phases collected, dried over $MgSO_4$, and the solvents removed under vacuum. The white solid was purified by silica flash column chromatography (1:4 diethyl ether:dichloromethane), 95% yield.

$^1$H NMR (400 MHz, $CDCl_3$-$d_6$): δ 5.60 (m, 1H); 3.75 (m, 1H); 3.26 (m, 1H); 2.09-2.13 (m, 2H); 1.18 (s, 6H); 1.21 (s, 3H); 1.10 (s, 3H); 0.80 (s, 3H).

Examples Based on Formula II

Example 10

UC2021-3β-ethynyl, 3α-hydroxyl, androstan-17-one

3β-ethynyl, 3α-hydroxyl, androstan-17-one 3, 17 androstandione (5.0 mmol) was dissolved in 50 mL dry THF at rt under nitrogen. Ethynyl magnesium bromide (1.1 equiv) was added dropwise at rt under stirring and the solution was left stirring overnight at rt under nitrogen flow.

The solution was then quenched with saturated $NH_4Cl$(aq) and the aqueous phase extracted with dichloromethane (3×30 mL). The collected organic phases were evaporated under reduced pressure, the resulting yellow oil dissolved in dichloromethane, washed with brine and dried over $MgSO_4$. The solution was reduced under vacuum, and the residue purified by silica flash column chromatography (1:4 diethylether: dichloromethane), typical yields 8%. Eventual traces of byproducts can be eliminated by further recrystallization from diethylether.

1H NMR (400 MHz, CDCl3-d6): δ 2.43-2.47 (s, 1H); 2.42 (m, 1H); 2.10-2.04 (m, 2H); 1.02 (m, 1H); 0.86 (s, 3H); 0.83 (s, 3H).

3αethynyl, 3βhydroxyl, androstane-17-one

Was obtained as a byproduct from the above described reaction and separated by preparative HPLC chromatography. Typical yield 65%.

1H NMR (400 MHz, $CDCl_3$-d6): δ 2.47 (s, 1H); 0.86 (s, 3H), 0.83 (s, 3H).

Example 11

UC2025-3β-ethynyl, 3α-hydroxyl, androstan-17-one oxime

3β-ethynyl, 3α-hydroxyl, androstan-17-one (10 mmol) is dissolved in dichloromethane 5 mL and ethanol 50 mL at rt and air atmosphere, in a 250 mL round bottom flask. 4 equiv. of $NH_2OH$ chlorhydrate and 4 equiv. of sodium acetate are dissolved in 5 mL $H_2O$ and then added to the steroid solution. 20 mL of ethanol are added and the mixture put on reflux overnight. The mixture is then cooled and the solvent removed under reduced pressure. The white residue is then treated with 50 mL $H_2O$ and 50 mL dichloromethane, the aqueous phase extracted with 3×30 mL dichloromethane. The collected organic phases are then dried over $MgSO_4$, filtrated and the solvent removed under reduced pressure. The final residue is purified by silica flash column chromatography dichloromethane:diethyl ether 4:1, typical yields 95-100% (quantitative).

1H NMR (400 MHz, CDCl3-d6): δ 2.56-2.41 (m, 2H); 2.43 (s, 1H); 1.87 (m, 2H); 1.00 (m, 1H); 0.80 (m, 1H); 0.90 (s, 3H), 0.83 (s, 3H).

Example 12

UC2027-3α-ethynyl, 3β-hydroxyl, androstan-17-one oxime

The title compound is obtained with the same procedure described for UC2025, starting from the corresponding 3α ethynyl, 3β hydroxyl, androstan-17-one, which is obtained as a by-product from the reaction described for the synthesis of UC2021.

$^1$HNMR (400 MHz, $CDCl_3$-$d_6$): δ 2.51-2.47 (m, 2H); 2.48 (s, 1H); 1.00 (m, 1H); 0.80 (m, 1H); 0.90 (s, 3H), 0.83 (s, 3H).

The invention claimed is:

1. A compound which is 3α-ethynyl, 3β-hydroxyl, androstan-17-one oxime or a pharmaceutically acceptable salt thereof.

2. A pharmaceutical composition comprising a compound according to claim 1 and a pharmaceutically acceptable carrier.

* * * * *